(12) United States Patent
Voic

(10) Patent No.: US 9,949,751 B2
(45) Date of Patent: Apr. 24, 2018

(54) ULTRASONIC DEBRIDER PROBE

(71) Applicant: MISONIX, INCORPORATED, Farmingdale, NY (US)

(72) Inventor: Dan Voic, Cedar Grove, NJ (US)

(73) Assignee: MISONIX, INC., Farmingdale, NY (US)

( * ) Notice: Subject to any disclaimer, the term of this patent is extended or adjusted under 35 U.S.C. 154(b) by 156 days.

(21) Appl. No.: 14/172,566

(22) Filed: Feb. 4, 2014

(65) Prior Publication Data
US 2015/0216549 A1 Aug. 6, 2015

(51) Int. Cl.
*A61B 17/32* (2006.01)
*A61B 17/00* (2006.01)

(52) U.S. Cl.
CPC ........... *A61B 17/320068* (2013.01); *A61B 2017/00761* (2013.01); *A61B 2017/320072* (2013.01)

(58) Field of Classification Search
CPC .......... A61B 17/320068; A61B 17/322; A61B 17/32; A61B 17/22012; A61B 17/22004; A61B 2017/320004; A61B 2017/320008; A61B 2017/320012; A61B 2017/00761; A61B 17/50; A61B 17/54; A61B 2017/320072
See application file for complete search history.

(56) References Cited

U.S. PATENT DOCUMENTS

| | | | |
|---|---|---|---|
| 3,823,717 A | 7/1974 | Pohlman et al. | |
| 5,674,234 A * | 10/1997 | McCool | A61B 17/32093 30/32 |
| 7,931,611 B2 | 4/2011 | Novak et al. | |
| 8,025,672 B2 | 9/2011 | Novak et al. | |
| 8,353,912 B2 | 1/2013 | Darian et al. | |
| 8,430,897 B2 | 4/2013 | Novak et al. | |
| 2006/0004396 A1 * | 1/2006 | Easley | A61B 17/1659 606/169 |
| 2008/0058775 A1 * | 3/2008 | Darian | A61B 17/320068 606/1 |
| 2008/0300591 A1 | 12/2008 | Darian et al. | |

(Continued)

FOREIGN PATENT DOCUMENTS

EP 0456470 A1 11/1991
WO WO2008/038307 4/2008

OTHER PUBLICATIONS

"Sonicone O.R. Ultrasonic Surgical Debridement" Misonix, Inc. 2012, p. 1 fig.

*Primary Examiner* — Melanie Tyson
(74) *Attorney, Agent, or Firm* — R. Neil Sudol; Henry D. Coleman

(57) ABSTRACT

An ultrasonic surgical instrument has a shaft and a probe head, the shaft and the probe head have a lumen or channel and a longitudinal axis and the probe head having a distal end face. The probe head has at least one operative surface engageable with organic tissues for the application of ultrasonic vibratory energy to the tissues. The end face is oriented at least partially transversely to the axis. The lumen or channel has a first outlet opening in the end face and at least one second outlet opening in a lateral surface of either the shaft or the probe head at a position spaced from the end face. The probe head has a plurality of teeth extending laterally from the end face, in two rows on opposing side of the end face.

18 Claims, 1 Drawing Sheet

(56) References Cited

U.S. PATENT DOCUMENTS

2014/0012261 A1\* 1/2014 Nita .................. A61B 17/1631
606/79
2014/0188095 A1\* 7/2014 Weber .................... A61B 18/24
606/15

\* cited by examiner

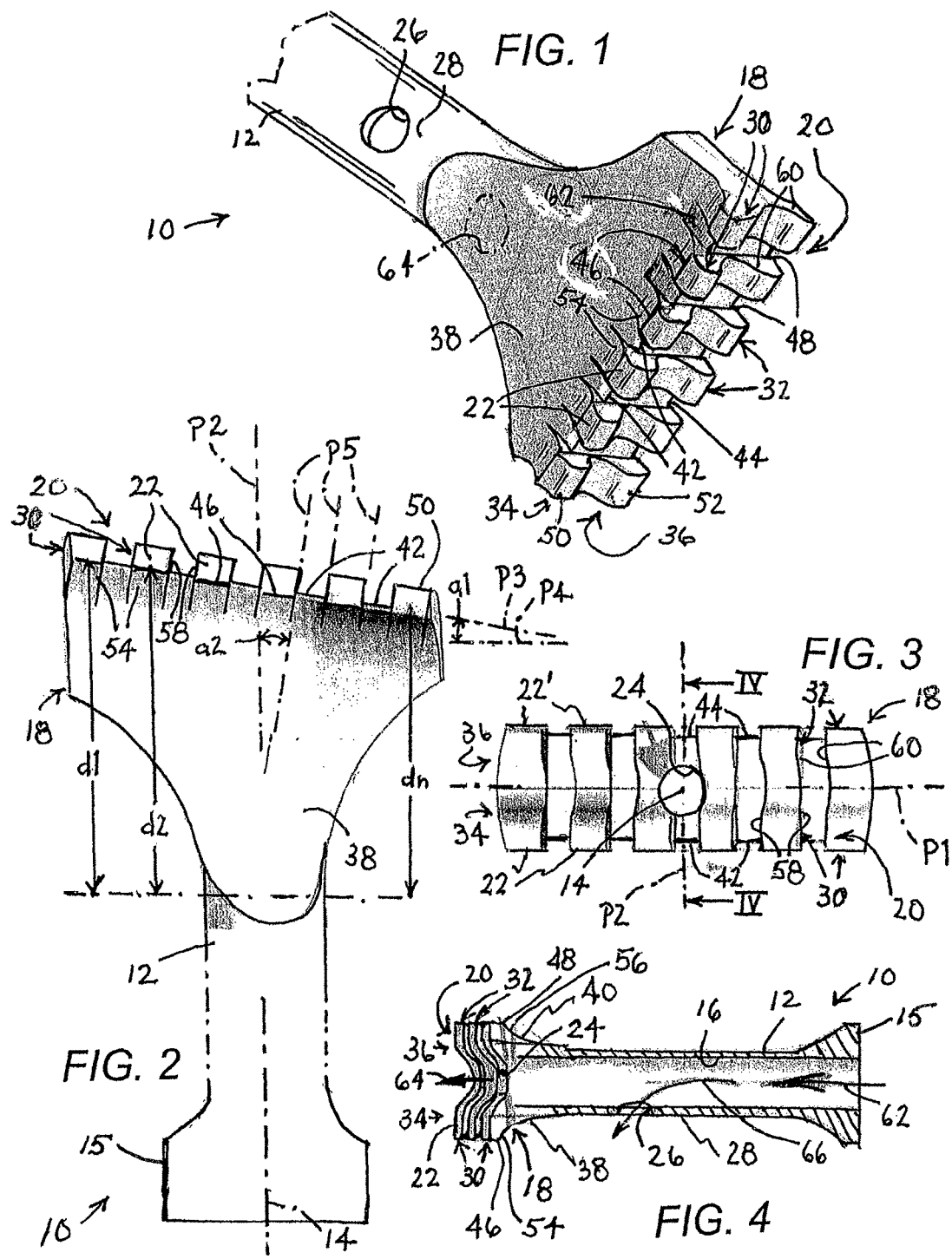

ULTRASONIC DEBRIDER PROBE

BACKGROUND OF THE INVENTION

This invention relates to an ultrasonic surgical instrument. More particularly, this invention relates to a high-efficiency medical treatment probe for use in wound debridement.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as micro streaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under the target tissue to separate it from the surrounding structure. The surgeon can then lift the tissue out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis, as shown in FIG. 1. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

U.S. Pat. No. 7,931,611 discloses an ultrasonic wound debrider probe with a central bore coincident with the longitudinal axis. The proximal end of said bore communicates with a bore in the ultrasonic handpiece using methods well known to the art, such as a male/female thread combination. The probe is shaped such as to provide both a resonant frequency of operation in the range for which the electronic generator was designed and an amplitude of vibration at the distal face which is desired for proper tissue ablation. Such amplitudes have generally been shown to be in the range of 30 to 300 microns. Probe heads or ends as disclosed in U.S. Pat. No. 7,931,611 incorporate either a substantially symmetrical distal end or a distal end with a pronounced asymmetry. Each end has attributes that increase its effectiveness on varying tissue pathologies. Probe ends may be further modified to improve the liquid flow to the probe/tissue interface such as to reduce the bulk temperature rise of the tissue and prevent clogging of the liquid passageway. Probe ends may also be modified to produce energy directors that impart energy from the sides of the probes instead of only at the distal face of the probe. Such energy directors, when contacting skin or tissue, will increase volume of tissue treated per unit time and thereby reduce the operating time of the procedure. In one specific embodiment of U.S. Pat. No. 7,931,611, an ultrasonic medical probe has an elongate shaft which is formed integrally with a head portion having a distal end face oriented at least partially transversely to a longitudinal axis of the shaft. The shaft is provided with an internal longitudinal channel or bore extending to the end face. The end face is formed with an indentation communicating with the channel or bore at a distal end thereof, whereby liquid is guided over an extended surface of the end face relative to the channel or bore. The head portion may be enlarged in a transverse direction relative to the shaft. In that event, the end face has an elongated shape, while the indentation is elongate and forms a groove in the end face of the head portion. This groove may extend parallel to or in a length dimension of the end face.

A problem that sometimes arises with convention wound debrider and other ultrasonic surgical tools is that the irrigation channel or bore, which may be intermittently connected to a suction source, sometimes becomes clogged with tissue, thus reducing the effectiveness of irrigation and/or aspiration.

OBJECTS OF THE INVENTION

An object of the present invention is to provide an improved ultrasonic surgical instrument for use in debridement of wounds.

A more particular object of the present invention is to provide such an instrument in the form of a probe that may be used in conjunction with ultrasonic surgical aspirators to debride wounds.

It is a more specific object of the present invention is to provide such an improved ultrasonic surgical instrument with improved irrigation or suction capability.

Another specific object of the present invention is to provide such an improved ultrasonic surgical instrument with improved tissue removal capability.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A probe for use as an ultrasonically vibrating tool in accordance with the present invention has a central bore coincident with a longitudinal axis of the probe shaft. The proximal end of the bore communicates with a bore in an ultrasonic handpiece using methods well known to the art, such as a male/female thread combination. The probe is shaped such as to provide both a resonant frequency of operation in the range for which the electronic generator was designed and an amplitude of vibration at the distal face which is desired for proper tissue ablation. Such amplitudes have generally been shown to be in the range of 30 to 300 microns. Again, the technique needed for calculating said shapes is well known to the art and outside the scope of this disclosure.

An ultrasonic surgical instrument in accordance with the present invention comprises (a) a shaft having a lumen or channel and a longitudinal axis and (b) a probe head disposed at a distal end of the shaft, the probe head having a distal end face. The probe head has at least one operative surface engageable with organic tissues for the application of ultrasonic vibratory energy to the tissues. The end face is oriented at least partially transversely to the axis and may be oriented perpendicularly to the axis. The lumen or channel has a first opening or port in the end face and at least one second opening or port in a lateral surface of either the shaft or the probe head at a position spaced from the end face.

Also in accordance with the present invention, an ultrasonic surgical instrument comprises a shaft having a longitudinal axis and a probe head disposed at a distal end of the shaft, the probe head having a distal end face oriented at least partially transversely to the axis, the probe head having a plurality of teeth extending laterally from the end face.

Preferably, the probe head is wider than the shaft, extends to opposite sides of the axis, and is formed with a pair of opposed lateral surfaces extending from a distal end of the shaft to the end face. The instrument axis is disposed in a plane bisecting the end face, while the lateral surfaces of the probe head are spaced from that plane. The teeth extend away from the plane generally orthogonally thereto.

Pursuant to another feature of the present invention, the teeth are disposed in two rows each along an opposite edge of the end face, the teeth of one of the rows projecting in a direction opposed to the teeth in the other of the rows.

Preferably, the end face is slanted or inclined relative to the axis so that the teeth in any one of the rows are disposed at different distances from the shaft. The teeth of either row are thus disposed in a linear array that is slanted or inclined relative to any plane that is perpendicular to the axis.

In accordance with another feature of the present invention, the teeth have operative surfaces at free ends that are spaced laterally from the axial plane (and may be oriented parallel thereto), the operative surfaces being defined on a proximal side by respective sharp edges. Where the end face of the probe head is slanted or inclined relative to the shaft axis so that the teeth are disposed in respective linear arrays each slanted or inclined relative to any plane perpendicular to the axis, the sharp edges of the teeth of either row are likewise linearly arranged.

In operation of the instrument, the operative surfaces or the teeth of on or the other row are placed into contact with a tissue surface at a surgical site. During subsequent ultrasonic vibration of the instrument, the sharp edges of the teeth are raked back and forth across the tissue surface, shaving tissue layers off from the operative site. The slanting of the teeth, relative to the direction of ultrasonic reciprocation (parallel to the axis of the instrument) results in a caroming action that moves the shaved tissue fragments towards the gaps between the teeth where the tissue fragments are subjected to suction force or aspiration applied through the channel port or opening in the end face of the probe head. That opening is preferably located centrally between the rows of teeth.

The sharp proximal edges of the teeth are preferably straight edges. It is to be noted that the teeth may be formed with sharp cutting edges alternatively or additionally on a distal side, opposite the hand piece and the probe shaft.

Pursuant to a more specific feature of the present invention, the probe head is further formed with a plurality of concave ramp surfaces equal in number to the teeth and each extending from one of the opposed lateral surfaces of the probe head to the sharp edge on the proximal side of a respective one of the teeth. Each tooth may be formed with a pair of planar lateral surfaces disposed parallel to one another and transversely to the sharp tooth edge(s). Those lateral tooth surfaces extend in planes oriented at a common acute angle relative to the axial plane that bisects the end face of the probe head. The present invention contemplates a surgical method utilizing an ultrasonic instrument having a head with a plurality of mutually spaced teeth along a distal end face of the head. The method generally comprises manipulating the instrument to press the teeth against organic tissue at a surgical site. While one maintains the teeth in contact with the tissue at the surgical site, vibratory energy is applied to the instrument and the instrument is pulled across the surgical site, whereby tissue fragments are shaved from the surgical site in a raking action.

The method typically includes delivering irrigation fluid via a channel in the instrument to the tissues at the surgical site at least in part during the applying of ultrasonic vibratory energy to the instrument and the pulling of the instrument across the surgical site. Subsequently severed tissue fragments are aspirated through the channel from the surgical site. The shaved tissue fragments are moved towards gaps between the teeth during the pulling of the instrument across the surgical site, where the tissue fragments are subjected to suction force or aspiration via a port or opening in the distal end face of the instrument.

BRIEF DESCRIPTION OF THE DRAWINGS

FIG. 1 is a schematic partial perspective view of an ultrasonic surgical instrument, probe or tool in accordance with the present invention.

FIG. 2 is a side elevation view of a probe head of the instrument or tool of FIG. 1.

FIG. 3 is a front or distal end elevational view of the instrument or tool of FIGS. 1 and 2.

FIG. 4 is a longitudinal cross-sectional view, taken along line IV-IV in FIG. 3.

DETAILED DESCRIPTION

An ultrasonic surgical instrument 10, particularly utilizable in wound debridement, includes a shaft or shank 12 having a longitudinal axis 14 and a lumen or channel 16 (FIG. 4) coaxial with the axis. Shaft or shank 12 is provided at a proximal end with a connector 15 for coupling the shaft to an ultrasonic signal generator. Instrument 10 further includes a flattened probe head 18 disposed at a distal end of shaft 12, the probe head having a distal end face 20. Probe head 18 has a plurality of operative surfaces 22 engageable with organic tissues for the application of ultrasonic vibratory energy to the tissues. End face 20 is oriented at least partially transversely to longitudinal axis 14. Lumen or channel 16 extends through probe head 18 and has a first opening or port 24 (FIG. 4) in probe head end face 20. Lumen or channel 16 has at least one second opening or port 26 preferably in a lateral surface 28 of shaft 12 at a position spaced from probe head 18 and particularly end face 20 thereof. Openings or ports 26 and 26 are outlets when irrigation is applied via lumen or channel 16 and inlets in when aspiration or suction is applied.

As depicted in FIGS. 1 and 4, probe head 18 is wider than shaft 12 and is thus laterally enlarged relative to shaft 12. Probe head 18 extends to opposite sides of axis 14, and is bisected by a longitudinal plane P1 (FIG. 3) containing axis 14. Probe head 18 has a plurality of teeth 30 and 32 extending laterally from end face 20. Teeth 30 and 32 are disposed in respective rows or linear arrays 34 and 36 extending in parallel to one another as well as in parallel with plane P1. Tooth arrays 34 and 36 are spaced from plane P1 on opposite sides thereof. The teeth extend away from plane P1 generally orthogonally thereto. Probe head 18 is mirror symmetric about plane P1 and may additionally be mirror symmetric about a second longitudinal plane P2 (FIG. 3) containing axis 14 and oriented orthogonally or perpendicularly to place P1.

Probe head 18 is defined in part by a pair of opposed major lateral surfaces 38 and 40 extending from a distal end of shaft 12 to end face 20 and more particularly to teeth 30 and 32. More particularly, major lateral surfaces 38 and 40 flare outwardly from the distal end of shaft 12 to end face 20 and extend at their distal ends to teeth 30 and 32 and to a plurality of edges 42 and 44 of end face 20 which are located between adjacent teeth 30 and 32 at the bases or roots thereof.

As shown in FIG. 2, end face 20 is disposed in a plane P3 that is slanted or inclined at an angle a1 relative to a transverse plane P4 that is perpendicular to axis 14. The different teeth 30 of row or array 34, as well as the teeth 32 or row or array 36, are disposed at different distances d1, d2, . . . dn from shaft 12. Tooth rows or arrays 34 and 36 are slanted or inclined relative to any plane (like plane P4) that is perpendicular to axis 14.

It is to be noted that angle a1 may be zero, in which case teeth 30 are all disposed at the same distance from the distal end of shaft 12. In general, angle a1 may take on any value between 0 and about 30 degrees.

Operative surfaces 22 and 22' are located at free ends of teeth 30, 32 and are spaced laterally from axial plane P1. Operative surfaces 22 and 22' are exemplarily oriented parallel to plane P1. Operative surfaces 22, 22' are defined on a proximal side by respective sharp edges 46 and 48. Opposed major lateral surfaces 38 and 40 of probe head 18 are contiguous with and defined at their distal end by edges 46 and 48. Owing to the slanting or inclination of end face 20 (as plane P3) relative to shaft axis 14, edges 46 and 48 of teeth 30 and 32 are likewise linearly arranged.

In operation of the instrument, irrigation fluid such as a saline solution is delivered to tissues at a surgical site via channel 16, and openings or ports 24 and 26, as indicated by arrows 162, 164, and 166 when either teeth 30 or teeth 32, and more particularly when either operative surfaces 22 or 22', are placed into contact with a tissue surface at a surgical site. During subsequent ultrasonic vibration of the instrument 10, sharp edges 46 or 48 of teeth 30 or 32 are raked back and forth across the tissue surface, shaving tissue layers off from the operative site. The slanting of the teeth, relative to the direction of ultrasonic reciprocation (parallel to the axis of the instrument) results in a camming action that pushes the shaved tissue fragments towards the gaps (not separately designated) between the teeth, defined by inter-tooth edges 42 or 44, where the tissue fragments are subjected to suction force or aspiration via port or opening 24 in probe end face 20. Owing to the symmetries of probe head 18 and more specifically end face 20, opening 24 is located at the geometrical center, on axis 14, between the rows 34 and 36 of teeth 20 and 32.

Cutting edges 46 and 48 of teeth 30 and 32 are preferably, but not necessarily, straight edges. Teeth 30 and 32 may be alternatively or additionally formed with sharp cutting edges on their distal sides 50 and 52, opposite the hand piece (not shown) and probe shaft 12.

Probe head 18 includes a plurality of concave ramp surfaces 54 and 56 each partially defining a respective tooth 30 or 32 and each extending from one of the opposed lateral surfaces 38 and 40 of probe head 18 to the sharp edge 46 or 48 on the proximal side of the respective tooth 30 or 32. Each tooth 30 and 32 may be formed with a respective pair of planar lateral surfaces 58 and 60, all disposed parallel to each other and transversely to the sharp tooth edges 46 and 48. Lateral tooth surfaces 58 and 60 extend in planes P5 oriented at a common acute angle a2 relative to axial plane P2 (which bisects end face 20).

Probe head 18 further includes a plurality of extension surfaces 62 which are interleaved or alternating with concave tooth-defining surfaces 54 and 56 and which are contiguous with, or ending at, respective inter-tooth edges 42 and 44 of end face 20.

In being provided with an ancillary irrigation and suction port 26 disposed in shaft 12 or possibly lateral surface 38 and/or 40, instrument 10 is more likely to enable continued irrigation of a surgical site if the main irrigation port 24 is blocked or occluded by severed organic tissue.

Although the invention has been described in terms of particular embodiments and applications, one of ordinary skill in the art, in light of this teaching, can generate additional embodiments and modifications without departing from the spirit of or exceeding the scope of the claimed invention. For instance, it is contemplated that an opening or port 64 of channel 16 could be located in a lateral surface of probe head 18, rather than or in addition to port 26 in shaft 12. Accordingly, it is to be understood that the drawings and descriptions herein are proffered by way of example to facilitate comprehension of the invention and should not be construed to limit the scope thereof.

What is claimed is:

1. An ultrasonic surgical instrument comprising:
a shaft having a lumen or channel and a longitudinal axis; and
a probe head disposed at a distal end of said shaft, said probe head being laterally enlarged with respect to said shaft and extending in a plane containing said axis, said probe head having a distal end face, said probe head having at least one operative surface engageable with organic tissues for the application of ultrasonic vibratory energy to said tissues, said end face being oriented at least partially transversely to said axis, said lumen or channel having a first opening or port in said end face, said lumen or channel having at least one second opening or port in a lateral surface of one of said shaft and said probe head at a position spaced from said end face, said probe head having two linear arrays of teeth, said arrays extending parallel to one another, said teeth extending in part laterally from said end face and away from said plane generally orthogonally thereto, said arrays each being located at and along an edge of said end face.

2. The instrument defined in claim 1 wherein said arrays are disposed along opposite edges of said end face, the teeth of one of said arrays projecting in a direction opposed to the teeth in the other of said arrays.

3. The instrument defined in claim 2 wherein said end face is slanted or inclined relative to said axis so that the teeth in any one of said arrays are disposed at different distances from said shaft.

4. The instrument defined in claim 3 wherein said teeth have operative surfaces at free ends spaced laterally from said axis, said teeth having respective sharp edges, said operative surfaces being defined on a proximal side by respective ones of said sharp edges.

5. The instrument defined in claim 4 wherein said sharp edges are straight edges.

6. The instrument defined in claim 5 wherein said probe head extends to opposite sides of said axis, said probe head being formed with a pair of opposed lateral surfaces extending from a distal end of said shaft to said end face, said probe head being further formed with a plurality of concave ramp surfaces equal in number to said teeth and each extending from one of said opposed lateral surfaces to the straight edge of a respective one of said teeth.

7. The instrument defined in claim 4 wherein said teeth each have a pair of planar lateral surfaces disposed parallel to one another, said lateral surfaces extending in planes oriented at a common acute angle relative to said axis.

8. The instrument defined in claim 7 wherein said probe head extends to opposite sides of said axis, said probe head being formed with a pair of opposed lateral surfaces extending from a distal end of said shaft to said end face, said probe head being further formed with a plurality of concave ramp surfaces equal in number to said teeth and each extending from one of said opposed lateral surfaces to the sharp edge of a respective one of said teeth.

9. An ultrasonic surgical instrument comprising:
a shaft having a longitudinal axis; and
a flattened probe head disposed at a distal end of said shaft, said probe head having a distal end face oriented at least partially transversely to said axis,
said probe head being laterally enlarged with respect to said shaft and having two major lateral faces extending in respective planes parallel to one another and said axis,
said probe head having a plurality of teeth extending in a linear array at and along an edge of said end face, in part laterally from said end face and away from a respective one of said major lateral faces and the respective one of said planes generally orthogonally thereto,
said shaft being provided with a lumen or channel having an opening or port in said end face.

10. The instrument defined in claim 9 wherein said probe head extends to opposite sides of said axis, said major lateral surfaces extending from a distal end of said shaft to said end face.

11. The instrument defined in claim 10 wherein said teeth are disposed in two linear arrays each along an opposite edge of said end face, the teeth of one of said arrays projecting in a direction at least partially opposed to the teeth in the other of said arrays.

12. The instrument defined in claim 11 wherein said end face is slanted or inclined relative to said axis so that the teeth in any one of said arrays are disposed at different distances from said shaft.

13. The instrument defined in claim 12 wherein said teeth have operative surfaces at free ends spaced laterally from both of said planes, said operative surfaces being defined on a proximal side by respective sharp edges.

14. The instrument defined in claim 13 wherein said sharp edges are straight edges.

15. The instrument defined in claim 14 wherein said probe head is further formed with a plurality of concave ramp surfaces equal in number to said teeth and each extending from one of said major lateral surfaces to the straight edge of a respective one of said teeth.

16. The instrument defined in claim 11 wherein said teeth each have a pair of planar lateral surfaces disposed parallel to one another, the teeth in either one of said linear arrays extending at a common acute angle relative to said major lateral surfaces and said planes.

17. The instrument defined in claim 9 wherein said teeth have respective operative surfaces engageable with organic tissues for the application of ultrasonic vibratory energy to said tissues, said lumen or channel having an opening or port in a lateral surface of one of said shaft and said probe head at a position spaced from said end face.

18. An ultrasonic surgical instrument comprising:
a shaft having a longitudinal axis; and
a flattened probe head disposed at a distal end of said shaft, said probe head having a distal end face oriented at least partially transversely to said axis, said shaft being provided at a proximal end with a connector for coupling said shaft to an ultrasonic signal generator,
said probe head being laterally enlarged with respect to said shaft and having two major lateral faces extending in respective planes parallel to one another and said axis,
said probe head having a plurality of teeth extending in a linear array at and along an edge of said end face, in part laterally from said end face and away from a respective one of said major lateral faces and the respective one of said planes generally orthogonally thereto.

* * * * *